United States Patent [19]
Gandi et al.

[11] 3,942,634
[45] Mar. 9, 1976

[54] TWO COMPARTMENT STERILANT PACKAGE

[75] Inventors: Robert A. Gandi, New York, N.Y.; Anthony P. Martino; Robert G. Pellegrino, both of Wayne, N.J.

[73] Assignee: Becton, Dickinson & Company, Rutherford, N.J.

[22] Filed: July 19, 1974

[21] Appl. No.: 490,021

[52] U.S. Cl. .................. 206/210; 21/58; 21/61; 21/109; 206/205; 206/438
[51] Int. Cl.² .............. A61L 13/00; A61L 13/02; B65D 83/00
[58] Field of Search ...... 21/58, 61, 109, 93, DIG. 4; 206/205, 210, 213, 390, 364, 438, 440; 229/56, 72

[56] References Cited
UNITED STATES PATENTS

| | | |
|---|---|---|
| 3,035,691 | 5/1962 | Rasmussen et al. ............ 206/364 |
| 3,494,726 | 2/1970 | Barasch .......................... 21/58 |
| 3,545,604 | 12/1970 | Gunther ........................ 53/36 X |
| 3,630,348 | 12/1971 | Benson et al. ................. 206/210 |
| 3,682,051 | 8/1972 | Sengewald .................... 206/390 |
| 3,698,549 | 10/1972 | Glassman ...................... 206/440 |
| 3,719,319 | 3/1973 | Schleutermann .............. 229/72 |

Primary Examiner—Morris O. Wolk
Assistant Examiner—Dale Lovercheck
Attorney, Agent, or Firm—Marn & Jangarathis

[57] ABSTRACT

Sterilant package comprised of first and second sheets of a gas barrier material and an intermediate sheet of paper having a material capable of releasing gaseous formaldehyde on heating, the sheets being sealed together to define the package, with the paper sheet being in the interior of the package. The paper sheet divides the package into two compartments.

9 Claims, 6 Drawing Figures

TWO COMPARTMENT STERILANT PACKAGE

This invention relates to a sterilant package, and more particularly a package in which articles can be sterilized.

Packages in which a material can be sterilized have been described in U.S. Pat. No. 3,494,726, granted on Feb. 10, 1970 and in U.S. Pat. No. 3,630,348, granted on Dec. 28, 1971. The present invention is directed to an improvement in sterilant packages of the type described in the aforementioned U.S. Patents.

In accordance with the present invention, there is provided a sterilant package comprised of two sheets of a gas barrier material and an intermediate paper sheet treated with a material capable of releasing gaseous formaldehyde on heating. The sheets are sealed together to define a sterilant package for receiving an article to be sterilized with the paper sheet being in the interior of the package.

In accordance with a preferred embodiment, the paper sheet forms an interior dividing wall thereby defining two separate and distinct compartments within the package, each of which can receive an article to be sterilized. In accordance with the preferred embodiment, each of the sheets of the gas barrier material is sealed at its periphery to opposite sides of the paper sheet, whereby articles can be separately removed from each of the compartments, without impairing the sterile integrity of the other compartment. The gas barrier sheets are preferably sealed to the paper sheet in a manner which provides a peelable seal to facilitate opening of the compartments.

The gas barrier sheets may be formed from any one of a wide variety of materials which are known to have a low vapor transmission level, such as polyethylene, polyesters, polypropylene, etc. The gas barrier sheets are preferably transparent, however, other materials, such as foil coated paper and various laminations can be used.

The paper sheet is treated with a material which releases gaseous formaldehyde on heating. Such materials are known in the art and representative examples of such materials are described in U.S. Pat. No. 3,630,348.

The coating material for releasing formaldehyde is preferably a compound having at least one $-CH_2-OR$ group capable of releasing gaseous formaldehyde on heating, wherein R is alkyl, preferably lower alkyl (1 to 6 carbon atoms), and most preferably R is methyl. A particularly preferred compound is hexamethoxymethylmelamine. The paper includes a sterilizing amount of such a compound, which is generally an amount to provide from about 0.1% to about 20%, by weight, of formaldehyde ($CH_2O$).

The invention will be further described with respect to the embodiments thereof illustrated in the accompanying drawing wherein.

Figure 1:
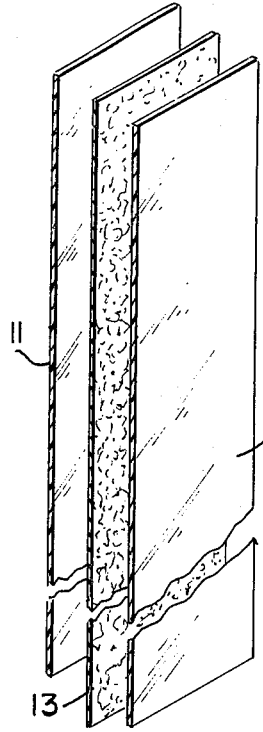
FIG. 1 is an isometric view of the sheets used in preparing the package of the present invention.
Figure 3:
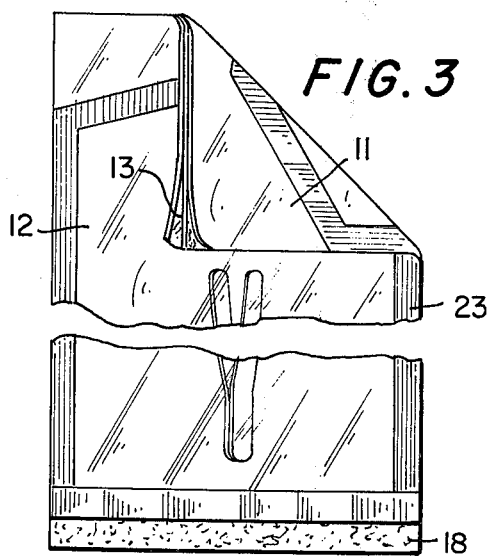
FIG. 3 is a front view, partially folded, of the package of FIG. 2.
Figure 2:
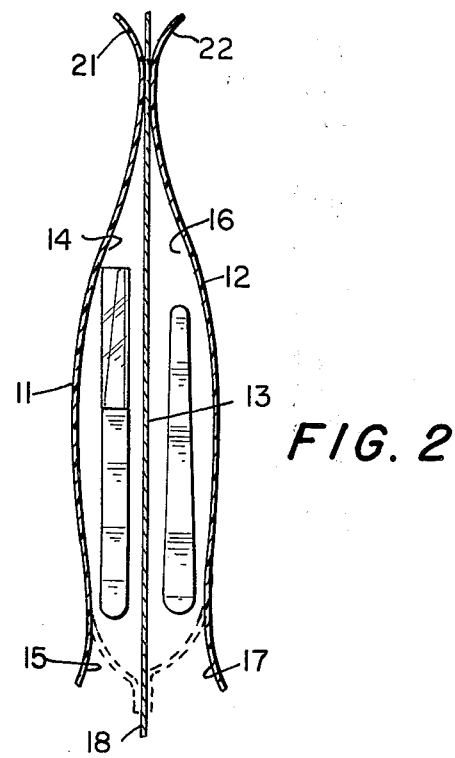
FIG. 2 is a cross section of an embodiment of the package of the present invention.

Referring to FIGS. 1–3 of the drawing, there is shown a sterilant package formed from a first film or sheet 11, formed of a gas barrier material, a second film or sheet 12, formed of a gas barrier material, and an intermediate paper sheet 13, which is treated with a material capable of releasing gaseous formaldehyde on heating. The sheets 11 and 12 are preferably provided with a peelable seal coating on the side to be sealed to the paper sheet 13 to maintain sterile integrity. The sealant material is such that the package can be opened by peeling without paper delamination, and without tearing the sheet. Such materials are well known in the art, and the selection of a particular material is well within the scope of those skilled in the art.

The sheet 11 is sealed, on three sides, to one side of the paper sheet 13, to define a first compartment 14, with an opening 15 through which an article to be sterilized can be inserted. Similarly, sheet 12 is sealed, on three sides to the other side of paper sheet 13 to define a second compartment 16, having an opening 17 for receiving an article to be sterilized. The paper sheet, at the open end of the package, preferably extends beyond the sheets 11 and 12 to provide a loading lip 18 for inserting the articles to be sterilized. The sheets 11 and 12, at the end opposite to the open end of the package, are sealed to the paper sheet 13 in a manner such that sheets 11 and 12 are provided with peel flaps 21 and 22, respectively, to facilitate opening of the package. As particularly shown, the peel flaps 21 and 22 are provided by sealing sheets 11 and 12 to sheet 13, inwardly from the peripheral edges at the end opposite to the open end.

Articles to be sterilized are inserted into compartments 14 and 16, and the openings 15 and 17 are closed, by sealing the sheets 11 and 12, respectively, at the open end, to the paper sheet 13 to provide a hermetic seal. A sealed package, containing articles in compartments 14 and 16 is illustrated in FIG. 3. The seal lines for the package are schematically indicated at 23.

The package can then be placed in a heated chamber to effect release of formaldehyde from the treated paper sheet 13, and thereby sterilize the articles in each of the compartments 14 and 16. The released formaldehyde is maintained in the compartments as result of the sealed gas barrier sheets 11 and 12.

A sterilized article can be removed from either compartments 14 and 16 by peeling one of the sheets 11 or 12 apart from the paper 13. The sheet 11 or 12 is preferably peeled by use of the peel flaps 21 or 22 respectively. As should be apparent, removal of an article from one of the chambers, in this manner, does not affect the integrity of the other chamber.

Figures 4, 5:
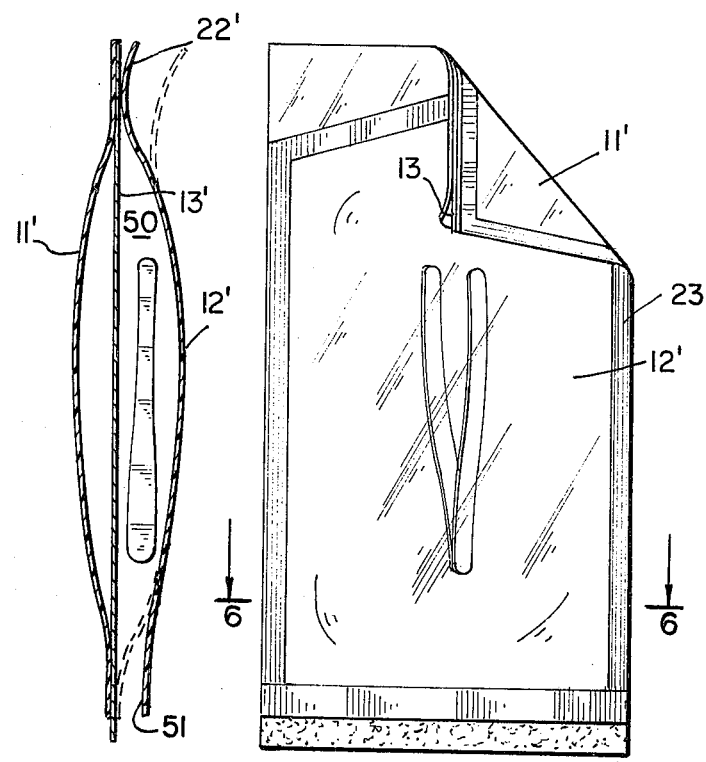
FIG. 4 is a cross section of another embodiment of the package of the present invention.
FIG. 5 is a front view, partially folded, of the package of FIG. 4.
Figure 6:
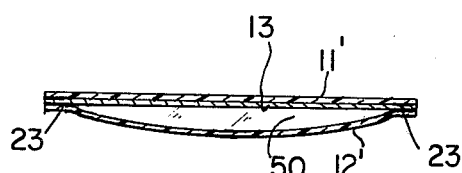
FIG. 6 is a section along 6—6 of FIG. 5.

Another embodiment of the present invention is illustrated in FIGS. 4–6 of the drawing. In the embodiment, illustrated in FIGS. 4–6, the package is formed with a single compartment 50 by sealing the sheet 11' to the paper sheet 13' on all four sides, and sealing the sheet 12', on three sides, to provide the compartment 50 with an opening 51 for receiving an article to be sterilized. The sheet 11' is sealed at its periphery, on all four sides, to paper sheet 13', whereas sheet 12' is sealed at three sides, with the side opposite the open side being sealed inwardly from the peripheral edge to provide a peel flap 22'.

As hereinabove described, with respect to the embodiment of the sterilant package illustrated in FIGS. 1 and 2, an article to be sterilized is inserted into the package through opening 51, and the opening closed by sealing the sheet 12' to paper 13' at the open end. The article is then sterilized in the package by application of heat, which releases formaldehyde from the treated paper sheet 13'.

The article may be removed from the package by peeling the sheet 11' from paper sheet 13', preferably by use of the peel flap 22'.

The packages of the present invention may be prepared individually or in roll form, as known in the art, whereby a package of the present invention can be torn from a roll, and an article to be sterilized is inserted into the open end thereof, followed by sealing of the package.

Numerous modifications and variations of the present invention are possible in light of the above teachings and, therefore, within the scope of the appended claims the invention may be practiced otherwise than as particularly described.

What is claimed is:

1. A sterilant package for articles to be sterilized, comprising:
    a first sheet of gas barrier material;
    a second sheet of gas barrier material; and
    a paper sheet, said paper sheet being treated with a material capable of releasing gaseous formaldehyde, said first sheet being sealed on three sides to a first face of the paper sheet to define a first sterilant compartment with a first opening for inserting a first article to be sterilized, said second sheet being sealed on three sides to a second face of the paper sheet to define a second compartment with a second opening for inserting a second article to be sterilized, said first and second sheets including a peelable seal coating for sealing a fourth side of each of said first and second sheets to the paper sheet to provide sealed first and second compartments for the first and second sterilant articles.

2. The sterilant package of claim 1 wherein the two compartments each contain an article to be sterilized and the first and second sheets are each sealed to the paper sheet to seal the two compartments.

3. The sterilant package of claim 2 wherein the first and second sheets are each sealed to the paper sheet by a peelable seal material.

4. The sterilant package of claim 4 wherein the first and second sheets are sealed to the paper sheet to provide first and second peel flaps for opening the two compartments.

5. The sterilant package of claim 1 wherein the first and second sheets are sealed to the paper sheet by a peelable seal material.

6. The sterilant package of claim 5 wherein the first and second sheets are sealed to the paper sheet to provide peel flaps for separately opening each of the two compartments.

7. The sterilant package of claim 6 wherein the paper sheet is treated with hexamethoxymethylmelamine.

8. The sterilant package of claim 6 wherein the first and second sheets are formed of a transparent material.

9. The sterilant package of claim 8 wherein the paper sheet at the openings to the two compartments extends beyond the first and second sheets to define a loading lip for inserting articles to be sterilized into the two compartments.

* * * * *